(12) United States Patent
Kelly et al.

(10) Patent No.: US 9,662,468 B2
(45) Date of Patent: May 30, 2017

(54) RESPIRATORY THERAPY SYSTEMS AND METHODS USING A GAS MIXING CIRCUIT

(71) Applicant: KONINKLIJKE PHILIPS N.V., Eindhoven (NL)

(72) Inventors: Eamonn Kelly, Carlsbad, CA (US); Romans Le Bang, Carlsbad, CA (US)

(73) Assignee: KONINKLIJKE PHILIPS N.V., Eindhove (NL)

( * ) Notice: Subject to any disclaimer, the term of this patent is extended or adjusted under 35 U.S.C. 154(b) by 364 days.

(21) Appl. No.: 14/345,670

(22) PCT Filed: Sep. 27, 2012

(86) PCT No.: PCT/IB2012/055142
§ 371 (c)(1),
(2) Date: Mar. 19, 2014

(87) PCT Pub. No.: WO2013/050907
PCT Pub. Date: Apr. 11, 2013

(65) Prior Publication Data
US 2014/0216455 A1   Aug. 7, 2014

Related U.S. Application Data

(60) Provisional application No. 61/543,437, filed on Oct. 5, 2011.

(51) Int. Cl.
*A61M 16/12* (2006.01)
*A61M 16/00* (2006.01)
(Continued)

(52) U.S. Cl.
CPC ...... *A61M 16/122* (2014.02); *A61M 16/0051* (2013.01); *A61M 16/0057* (2013.01);
(Continued)

(58) Field of Classification Search
CPC ............. A61M 16/122; A61M 16/057; A61M 16/0891; A61M 16/161; A61M 16/0833;
(Continued)

(56) References Cited

U.S. PATENT DOCUMENTS 3,714,944 A * 2/1973 Price ................. A61M 16/0465
128/203.12
5,335,653 A * 8/1994 Blomqvist ............. A61B 5/083
128/200.24
(Continued)

FOREIGN PATENT DOCUMENTS

DE    102004030747 A1 * 1/2006  ............. B01F 3/026
DE    102004040740 A1   2/2006
DE    202008057180 B3   4/2010
WO       9622803 A1     8/1996

*Primary Examiner* — Justine Yu
*Assistant Examiner* — Timothy Stanis (57) ABSTRACT

Systems and methods for mixing at least two gases for delivery to the airway of a subject use a gas mixing circuit having a diffusion portion. The diffusion portion may be configured to elongate the shape of the cross-section of the path through the gas mixing circuit in a particular direction and/or orientation. As a result, the gas concentration profile of the gas mixture after the gas mixing circuit is more uniform than the gas concentration profile after the merging of multiple gases.

18 Claims, 8 Drawing Sheets

(51) Int. Cl.
  *A61M 16/08* (2006.01)
  *A61M 16/16* (2006.01)
  *A61M 16/10* (2006.01)
(52) U.S. Cl.
  CPC .... *A61M 16/0069* (2014.02); *A61M 16/0833* (2014.02); *A61M 16/0891* (2014.02); *A61M 16/12* (2013.01); *A61M 16/125* (2014.02); *A61M 16/161* (2014.02); *A61M 2016/0027* (2013.01); *A61M 2016/0036* (2013.01); *A61M 2016/102* (2013.01); *A61M 2016/1025* (2013.01); *A61M 2202/0208* (2013.01); *A61M 2205/3365* (2013.01); *A61M 2205/3546* (2013.01); *A61M 2205/3576* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2206/12* (2013.01); *A61M 2206/14* (2013.01)

(58) Field of Classification Search
  CPC .............. A61M 16/0069; A61M 16/12; A61M 16/125; A61M 16/0051
  See application file for complete search history.

(56) References Cited

U.S. PATENT DOCUMENTS

| 5,522,381 | A | * | 6/1996 | Olsson | A61M 16/12 |
| | | | | | 128/203.12 |
| 5,605,148 | A | * | 2/1997 | Jones | A61M 16/12 |
| | | | | | 128/203.12 |
| 6,431,170 | B1 | | 8/2002 | Truitt | |
| 6,899,136 | B1 | * | 5/2005 | Stromberg | A61M 16/12 |
| | | | | | 137/625.4 |
| 2008/0190421 | A1 | * | 8/2008 | Zitting | A61M 16/12 |
| | | | | | 128/200.24 |

* cited by examiner

RESPIRATORY THERAPY SYSTEMS AND METHODS USING A GAS MIXING CIRCUIT

CROSS-REFERENCE TO PRIOR APPLICATIONS

This application is the U.S. National Phase application under 35 U.S.C. §371 of International Application No. PCT/IB2012/055142, filed on Sep. 27, 2012, which claims the benefit of U.S. Provisional Patent Application No. 61/543,437, filed on Oct. 5, 2011. These applications are hereby incorporated by reference herein.

BACKGROUND

1. Field

The present disclosure pertains to systems and methods for mixing breathable gases while providing respiratory therapy to a subject, and, in particular, to mixing flows of gas through diffusion such that the concentration profile of the resulting gas mixture is more uniform than the concentration profile at the point where the gas flows are merged.

2. Description of the Related Art

It is well known that respiratory therapy may be an important component of a therapeutic regimen of a subject. Respiratory therapy involving both invasive and non-invasive ventilation is well known. Measuring gas parameters of the flow of breathable gas delivered to the airway of a subject through a ventilator is well known. It is well known that respiratory therapy may include a mixture of breathable gases, e.g. including oxygen-enriched air. It may be known that merging gases may create a gas mixture having a non-uniform concentration profile. It may be known that sensor readings of measurements of gas parameters of a gas mixture having a non-uniform concentration profile may be inaccurate.

SUMMARY

Accordingly, it is an object of one or more embodiments of the present disclosure to provide a respiratory therapy system configured to mix at least two gases for delivery to the airway of a subject. The respiratory therapy system includes a pressure generator configured to generate a pressurized flow of a first gas for delivery to the airway of a subject, a gas coupler configured to fluidly couple the respiratory therapy system to a gas supply to transfer a second gas from the gas supply through the gas coupler, a gas merging circuit configured to merge the first gas from the pressure generator with the second gas from the gas supply into a gas mixture, and a gas mixing circuit. The gas mixture may have a first gas concentration profile after being merged by the gas merging circuit. The gas mixing circuit may be configured to mix the first gas with the second gas along a path of the gas mixing circuit. The gas mixing circuit may include an inlet configured to receive the gas mixture of the first gas and the second gas from the gas merging circuit, wherein a cross-section of the path at the inlet has a first shape, a diffusion portion configured to mix the first gas and the second gas through diffusion, wherein a cross-section of the path at the diffusion portion has a second shape that is elongated with respect to the first shape to enhance diffusion of the gas mixture as the gas mixture travels through the diffusion portion, and an outlet configured to receive the gas mixture that has been mixed within the diffusion portion, and to guide the gas mixture to a respiratory circuit for delivery to the airway of the subject. The gas mixture guided by the outlet may, by virtue of the mixing within the diffusion portion, have a second gas concentration profile that is more uniform than the first gas concentration profile.

It is yet another aspect of one or more embodiments of the present disclosure to provide a method for mixing at least two gases for delivery to the airway of a subject. The method may comprise providing a flow of a first gas to a first inlet of a gas merging circuit; fluidly coupling a second flow of a second gas to a second inlet of the gas merging circuit, at the same time as the provision of the flow of the first gas; receiving a gas mixture of the first gas and the second gas at an inlet of a gas mixing circuit, wherein the gas mixture has a first gas concentration profile at the inlet of the gas mixing circuit, and wherein a cross-section of the inlet has a first shape; diffusing the gas mixture from the inlet of the gas mixing circuit through a diffusion portion, wherein a cross-section of the diffusion portion has a second shape that is elongated with respect to the first shape to enhance diffusion of the gas mixture as the gas mixture travels through the diffusion portion; and delivering the gas mixture to a respiratory circuit for delivery to the airway of a subject. The delivered gas mixture may, by virtue of the diffusion, have a second gas concentration profile that is more uniform than the first gas concentration profile.

It is yet another aspect of one or more embodiments to provide a system configured for mixing at least two gases for delivery to the airway of a subject. The system may comprise: means for providing a flow of a first gas to a first inlet of a gas merging means; means for fluidly coupling a gas supply to the system to transfer a second flow of a second gas to a second inlet of the gas merging means, at the same time as the flow of the first gas is provided to the first inlet of the gas merging means; the gas merging means for generating, at a merging outlet, a gas mixture of the first gas provided at the first inlet and the second gas provided at the second inlet, wherein the gas mixture has a first gas concentration profile after being merged, and wherein a cross-section of the merging outlet has a first shape; means for diffusing the gas mixture from the merging outlet, wherein a cross-section of the means for diffusing has a second shape that is elongated with respect to the first shape to enhance diffusion of the gas mixture as the gas mixture travels through the means for diffusing; and means for delivering the gas mixture to a respiratory circuit for delivery to the airway of a subject. The delivered gas mixture may, by virtue of diffusion, have a second gas concentration profile that is more uniform than the first gas concentration profile.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals may designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
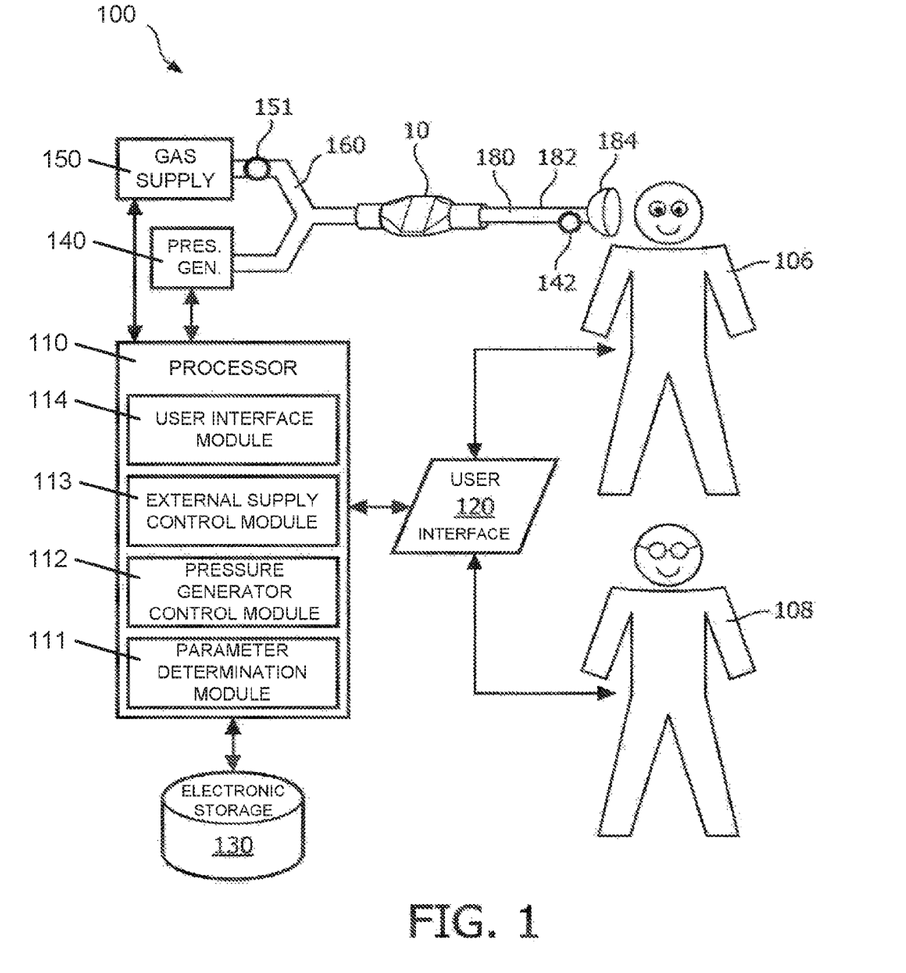
FIG. 1 schematically illustrates a respiratory therapy system configured to mix gases for delivery to the airway of a subject, in accordance with one or more embodiments.

FIG. 1 schematically illustrates a respiratory therapy system 100 configured to mix gases for delivery to the airway of a subject 106, in accordance with one or more embodiments. Respiratory therapy system 100 may be interchangeably referred to as system 100 herein. Mixing the gases into a (increasingly) uniform gas mixture allows an increasingly accurate measurement of a concentration of a gas and/or a gas component in a gas mixture. System 100 may include one or more of a pressure generator 140, a gas coupler 151, a gas merging circuit 160, a gas mixing circuit 10, a sensor 142, an electronic storage 130, a user interface 120, a subject interface 180, a processor 110, and/or other components. Note that although this disclosure describes mixing of gases, a structure similar to gas mixing circuit 10 may be used to mix liquids as well.

Pressure generator 140 (FIG. 1) is configured to provide a (pressurized) flow of breathable gas to the airway of subject 106, e.g. via gas merging circuit 160, gas mixing circuit 10, and subject interface 180. Subject 106 may initiate zero, one, or more phases of respiration. Pressure support through the pressurized flow of breathable gas may be implemented as a higher and lower positive pressure of a (multi-level) PAP device. For example, to support inspiration, the pressure of the pressurized flow of breathable gas is adjusted to an Inspiratory Positive Air Pressure (IPAP). Similarly, to support expiration, the pressure of the pressurized flow of breathable gas is adjusted to an Expiratory Positive Air Pressure (EPAP). Other schemes for providing respiratory support through the delivery of the pressurized flow of breathable gas, including but not limited to invasive and non-invasive ventilation, are contemplated. Note that a pressure level need not be constant throughout an entire phase of respiration.

Gas coupler 151 (FIG. 1) is configured to fluidly couple system 100 to a gas supply 150 to transfer a gas from gas supply 150 through gas coupler 151. In some embodiments, gas supply 150 supplies oxygen, oxygen-enriched air, and/or one or more other breathable gases or mixtures thereof. The gas transferred through gas coupler 151 may be merged with the flow of breathable gas provided by pressure generator 140 in gas merging circuit 160. Gas supply 150 may be configured such that the provided gas is pressurized.

Figure 3:
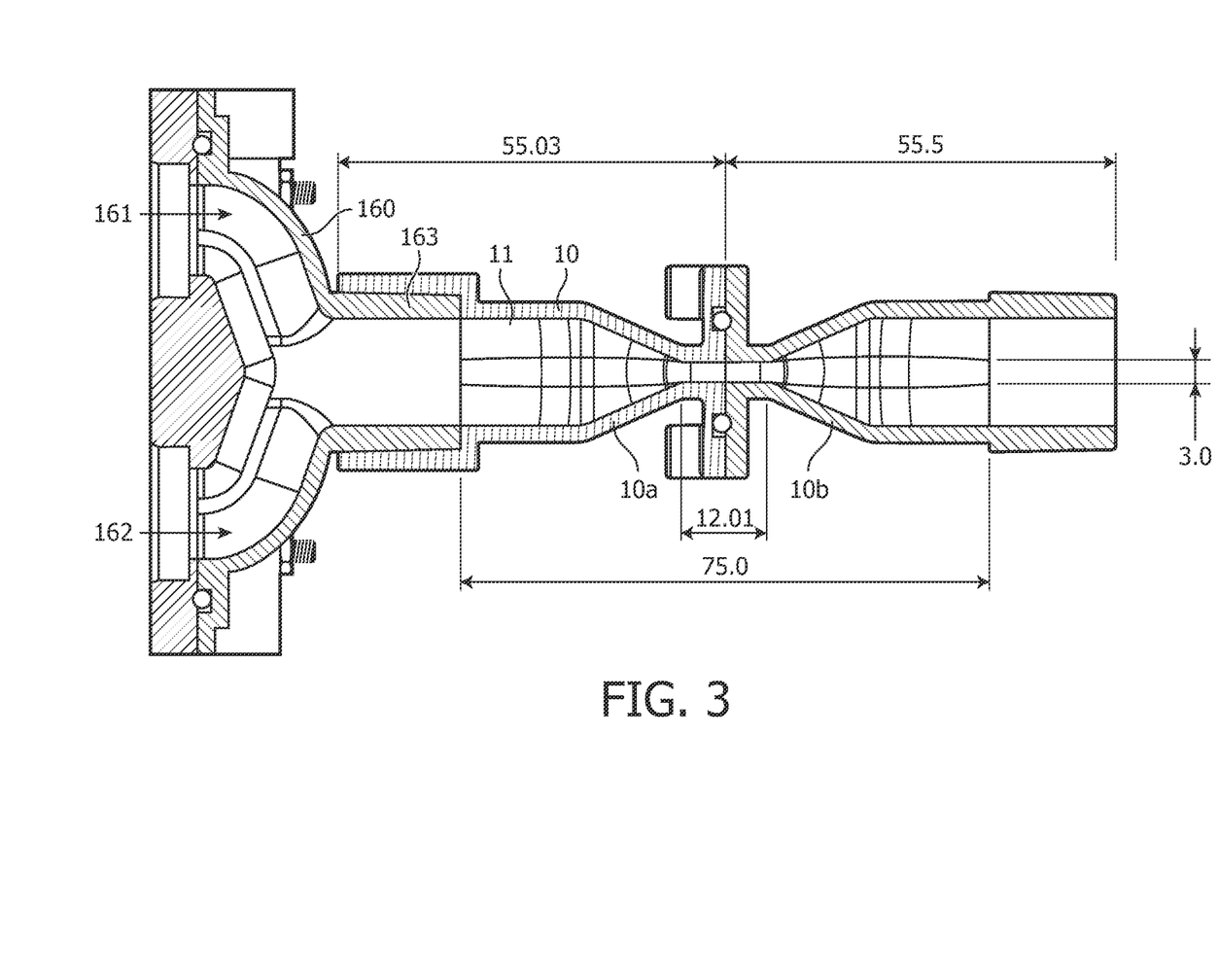
FIG. 3 illustrates a cross-sectional side view of part of a respiratory therapy system configured to mix gases.

Gas merging circuit 160 (FIG. 1) is configured to merge at least two flows of gas into a gas mixture. Gas merging circuit 160 may include at least two gas inlets, fluidly coupled, e.g., to pressure generator 140 and, via gas coupler 151, to gas supply 150, respectively. An outlet of gas merging circuit 160 may be fluidly coupled to gas mixing circuit 10 to transfer the gas mixture from gas merging circuit 160 to gas mixing circuit 10. A gas and/or a gas component in the gas mixture, as merged by gas merging circuit 160, may not have a uniform concentration. The first gas inlet of gas merging circuit 160 may be arranged relative to the second gas inlet of gas merging circuit 160 according to a merging orientation. By way of illustration, FIG. 3 illustrates a cross-sectional side view of part of system 100, in particular gas merging circuit 160 and gas mixing circuit 10. As depicted in FIG. 3, which is not intended to be limiting, the merging orientation of inlet 161 and inlet 162 is substantially vertical. As shown, the merging orientation of inlet 161 and inlet 162 may affect the orientation of a concentration profile of the gas mixture at outlet 163 of gas merging circuit 160. Outlet 163 may be fluidly coupled to inlet 11 of gas mixing circuit 10, which in some embodiments may be constructed from first gas mixing circuit half 10a and second gas mixing circuit half 10b. In FIG. 3, the depicted numbers having a decimal point (i.e. the italic numbers) represent suggested dimensions, in mm, of one or more embodiments of system 100. In some embodiments, gas merging circuit 160 may be configured to merge three or more flows of gas into a gas mixture.

Referring to FIG. 1 and the description of gas merging circuit 160, a concentration profile of a gas mixture and/or flow of gas may be a numerical and/or graphical representation indicating a level of homogeneity of the gas mixture and/or flow of gas. Alternatively, and/or simultaneously, the concentration profile may indicate the composition/percentage of one or more components within the gas mixture and/or flow of gas.

Figure 6:
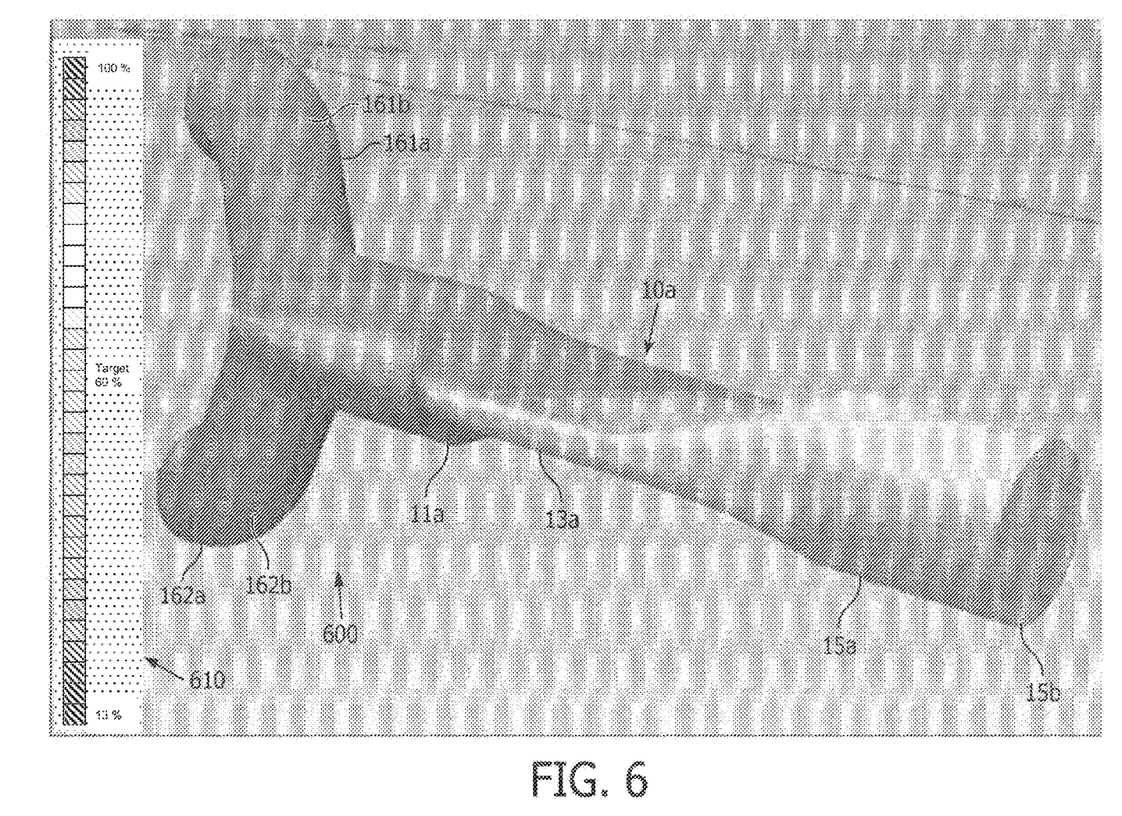
FIG. 6 illustrates a computational fluid dynamics (CFD) analysis of mixing two gases across part of a respiratory therapy system configured to mix gases.

As used herein, a concentration profile refers to the spatial distributions of relative concentrations of the gas flows being merged and/or mixed in gas merging circuit 160 and/or gas mixing circuit 10. By way of illustration, FIG. 6 depicts a spatial distribution 600 of a relative concentration of a gas flow being merged and/or mixed across a cross-section of gas merging circuit 160 and/or gas mixing circuit 10. In some embodiments, spatial distribution 600 corresponds to the spatial distribution of gas flows at or near the interface between gas merging circuit 160 and gas mixing circuit 10 (shown in FIG. 1 and described herein).

In spatial distribution 600, at a point 161b near the supply of gas containing mostly oxygen, the gas mixture contains mostly oxygen, whereas at a point 162b near the supply of ambient air, the gas mixture contains a (nearly) ambient-air-level percentage of oxygen, e.g. 21%. The reason the gas mixture does not have a uniform concentration is because generally two gases being merged will not instantaneously become uniformly distributed. The concentration of the gas mixture at a given spot in the cross-section depends on various factors, including the respective flow rates, directions of the gas flows at the point they are merged, relative flow rates, relative velocities, and/or other factors. Non-uniformity in the concentration profile of merged gas flows may, for example, lead to inaccurate measurements of concentration (e.g., since measurements are typically not sampled in a spatially dense manner), and/or cause other inaccuracies or drawbacks.

Referring back to FIG. 1, system 100 may be configured such that one or more gas parameters of the pressurized flow of breathable gas are controlled in accordance with a therapeutic respiratory regimen for subject 106. The one or more gas parameters include one or more of flow, volume, concentration (e.g. of oxygen), retrograde volume, pressure, humidity, velocity, acceleration, and/or other parameters. System 100 may be configured to provide types of therapy including types of therapy where a subject performs inspiration and/or expiration of his own accord or where the device provides negative airway pressure. In some embodiments, one or more gas parameters of the pressurized flow of breathable gas and/or the flow of gas through gas coupler 151 may be controlled through a feedback loop that is based, at least in part, on measurements performed downstream from gas merging circuit 160. For example, a sensor may be arranged after gas mixing circuit 10 to determine the oxygen percentage in the gas mixture, and this determination may be used to control the operation of system 100.

Figures 2A, 2C:
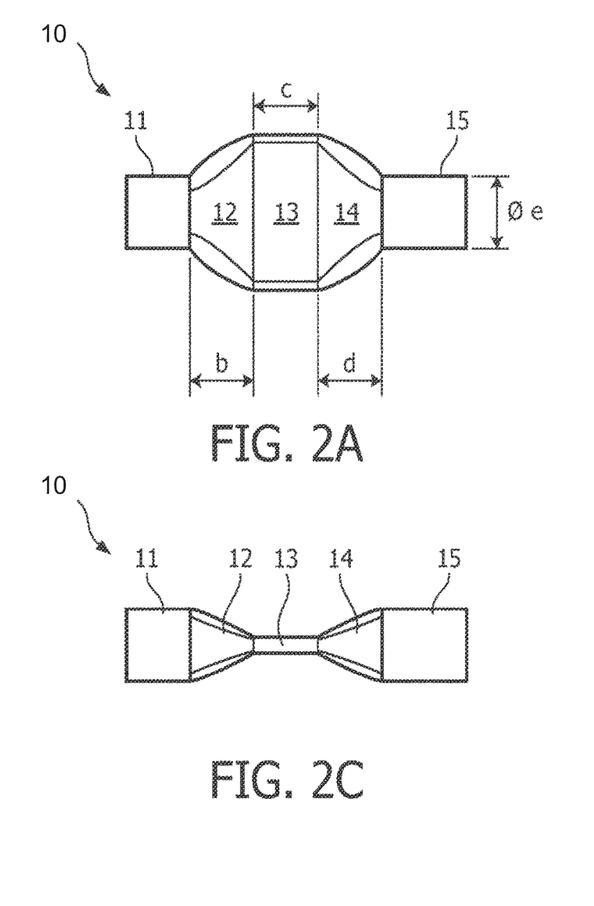
FIG. 2A-D illustrate various views of a gas mixing circuit according to one or more embodiments.

Gas mixing circuit 10 (FIG. 1) is configured to mix the gas mixture along a (three-dimensional) path formed within gas mixing circuit 10 such that the concentration profile becomes increasingly more uniform as the gas mixture travels through gas mixing circuit 10. Such mixing may be primarily or solely a result of diffusion within gas mixing circuit 10. Gas mixing circuit 10 may further be configured such that the pressure drop across gas mixing circuit 10 is less than about 10 cmH$_2$O, less than about 5 cmH$_2$O, less than about 15 cmH$_2$O, and/or another pressure drop for a gas mixture having a flow rate of about 200 Standard Liter Per Minute (SLPM), about 250 SLPM, and/or about 300 SLPM. Gas mixing circuit 10 may comprise one or more of inlet 11, a first transitional portion 12, a diffusion portion 13, a second transitional portion 14, an outlet 15, and/or other components. By way of illustration, FIG. 2A-D illustrates various views of gas mixing circuit 10. FIG. 2A shows a top-down plan view of gas mixing circuit 10. A gas or gas mixture may enter gas mixing circuit 10 at inlet 11, travel via first transitional portion 12 to diffusion portion 13, and proceed, via second transitional portion 14, to outlet 15.

Inlet 11 of gas mixing circuit 10 (FIG. 2A-D) is configured to receive the gas mixture from gas merging circuit 160. A cross-section of the path within inlet 11 has a first shape. The first shape may be circular, oval, triangular, square, rectangular, and/or any other shape. The first shape may have a maximum inlet diameter and a minimum inlet width. In the examples depicted in FIG. 2A-D, which are not intended to be limiting, inlet 11, as well as the path within inlet 11, may have a circular shape, such that the inlet diameter and inlet width may be substantially similar. For the purposes of this disclosure, the diameter and width of a planar shape are defined such that the diameter is at least as large as the width. For example, an oval is elongated such that its diameter is greater than its width.

First transitional portion 12 of gas mixing circuit 10 (FIG. 2A-D) is configured to fluidly couple inlet 11 to diffusion portion 13, and is further configured to gradually transform the shape of the path within gas mixing circuit 10. In FIG. 2A the depth of first transitional portion 12 is depicted as b. In some embodiments, depth b is about 15 mm.

Diffusion portion 13 of gas mixing circuit 10 (FIG. 2A-D) is configured to mix the gas mixture through diffusion. A cross-section of the path within diffusion portion 13 has a second shape. The second shape may be circular, oval, triangular, square, rectangular, and/or any other shape. The second shape is configured to be elongated with respect to the first shape of inlet 11, e.g. along a particular orientation, to enhance diffusion of the gas mixture as the gas mixture travels through diffusion portion 13. The second shape may have a maximum diffusion diameter and a minimum diffusion width. The maximum diffusion diameter may be at least twice the maximum inlet diameter. In some embodiments, the maximum diffusion diameter may be at least three times the maximum inlet diameter. The minimum diffusion width may be less than half the minimum inlet width. In some embodiments, the minimum diffusion width may be about three times smaller, about four times smaller, about five times smaller, and/or any number between two and ten times smaller than the minimum inlet width. In FIG. 2A the depth of diffusion portion 13 is depicted as c. In some embodiments, depth c is about 15 mm. Mixing gases through diffusion may be preferred to mixing gases through turbulence since diffusion may cause less pressure drop than turbulence. Though some amount of diffusion and turbulence may be unavoidable when transporting a gas mixture over any length, the shape and structure of gas mixing circuit 10 is configured to mix gases chiefly through diffusion.

The orientation of diffusion portion 13 of gas mixing circuit 10 (FIG. 2A-D) may be referred to as the diffusion orientation. The diffusion orientation may be transverse to the merging orientation. The diffusion orientation may be substantially perpendicular to the merging orientation, i.e. at an angle between 80 and 100 degrees rotated from each other. Alternatively, and/or simultaneously, in some embodiments, the gas concentration profile at or near inlet 11 may be characterized by including at least two areas: a first area defined by the highest quartile of the concentration of a particular gas or gas component in the gas mixture, and a second area defined by the lowest quartile of the concentration of the same particular gas or the same gas component in the gas mixture. The direction of a line through a centroid of the first area and a centroid of the second area may be defined as a merging orientation.

Second transitional portion 14 of gas mixing circuit 10 (FIG. 2A-D) is configured to fluidly couple diffusion portion 13 to outlet 15, and further configured to gradually transform the shape of the path within gas mixing circuit 10. In FIG. 2A the depth of second transitional portion 14 is depicted as d. In some embodiments, depth d is about 15 mm.

Figure 2B:
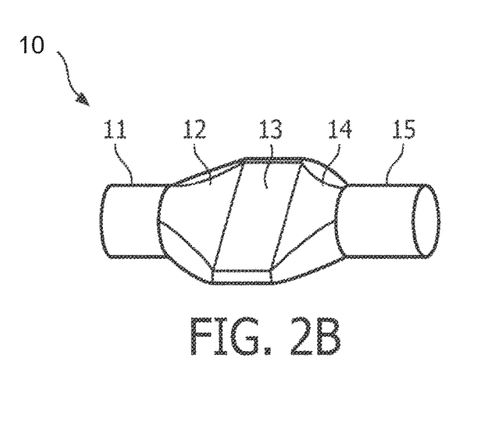
Figure 2D:
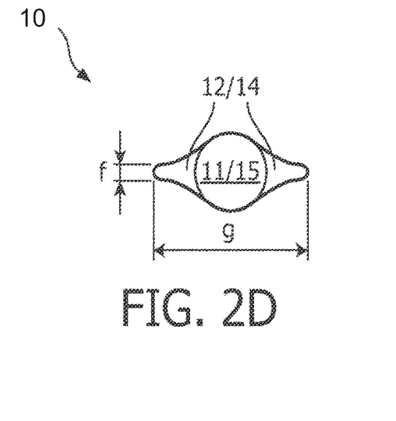
Figure 4:
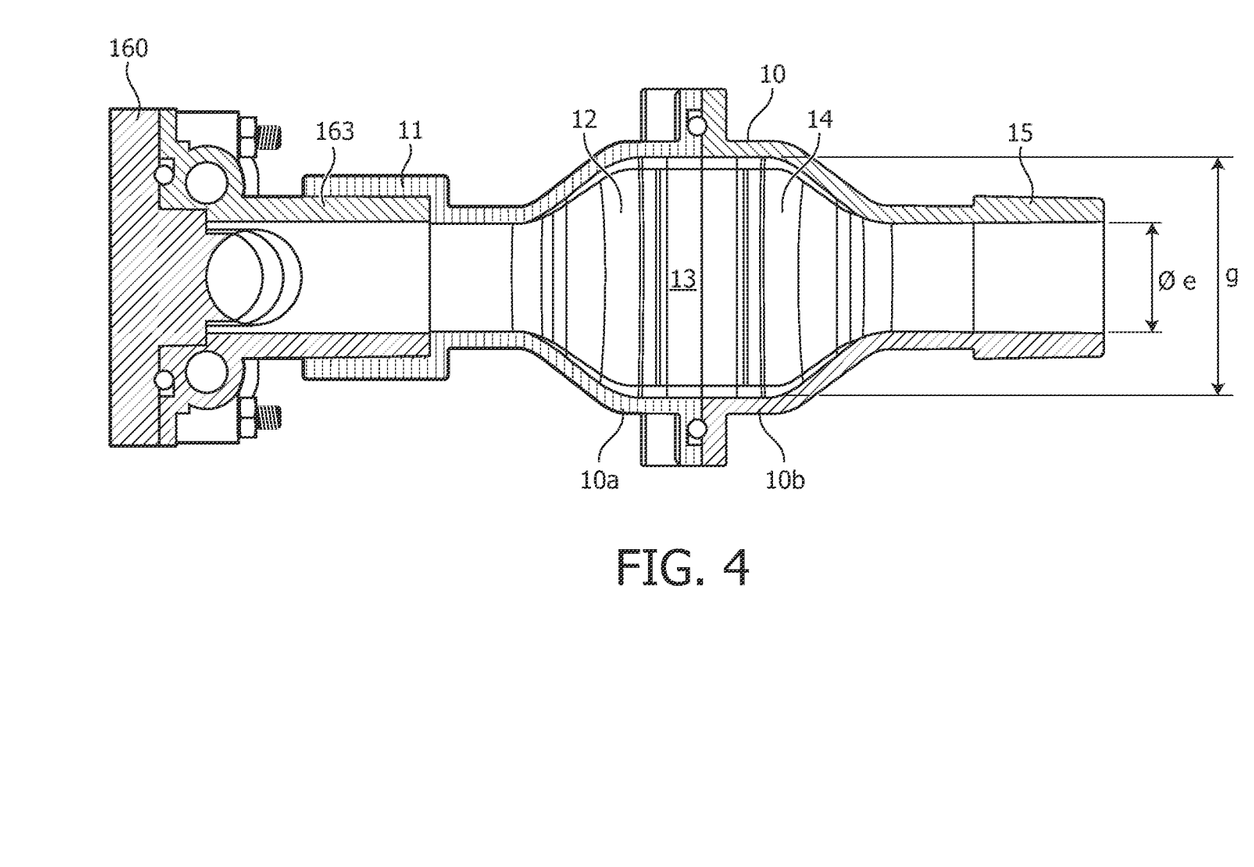
FIG. 4 illustrates a cross-sectional top-down view of part of a respiratory therapy system configured to mix gases.

Outlet 15 of gas mixing circuit 10 (FIG. 2A-D) is configured to receive the gas mixture, via second transitional portion 14, from diffusion portion 13 and guide the gas mixture to a respiratory circuit, such as, e.g., subject interface 180, for delivery to the airway of subject 106. In the examples depicted in FIG. 2A-D, outlet 15, as well as the path within outlet 15, may have a circular shape, such that transitional portion gradually transforms the second shape of diffusion portion 13 into the circular shape of outlet 15. In FIG. 2A the diameter of outlet 15 is depicted as e. In some embodiments, e is about 15 mm. FIG. 2B shows an isometric view of gas mixing circuit 10. FIG. 2C shows a cross-sectional side view of gas mixing circuit 10, cut along a longitudinal axis of gas mixing circuit 10. FIG. 2D shows either a front-to-back view or a back-to-front view of gas mixing circuit 10. In FIG. 2D the maximum diffusion diameter of diffusion portion 13 (implied but not shown through occlusion by first transitional portion 12 and/or second transitional portion 14) is depicted as g. In some embodiments, g is about 33 mm. In FIG. 2D the minimum diffusion width of diffusion portion 13 is depicted as f. In some embodiments, f is about 3 mm. By way of illustration, FIG. 4 illustrates a cross-sectional top-down view of part of system 100, showing, at least, first gas mixing circuit half 10a, second gas mixing circuit half 10b, diameter e of outlet 15, maximum diffusion diameter g of diffusion portion 13, and other components.

The ratio $R_{WD}$ of the diffusion diameter and the diffusion width may be about greater than 10, about 11, about 12, and/or another ratio. The ratio $R_{DW-IW}$ of the diffusion width and the inlet width may be no less than about 2, about 2.5, and/or another ratio.

Referring to FIG. 1, a pressurized flow of breathable gas is delivered from gas mixing circuit 10 to or near the airway of subject 106 by a subject interface 180. Subject interface 180 may include a conduit 182, a subject interface appliance 184, and/or other components. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and gas mixing circuit 10.

By way of illustration, FIG. 6 illustrates a computational fluid dynamics (CFD) analysis of mixing two gases across part of system 100, resulting in spatial distribution 600. In the analysis for FIG. 6, a flow 162a of 10 Standard Liter Per Minute (SLPM) of air (received through inlet 162) is merged and mixed with a flow 161a of 10 SLPM of oxygen (received through inlet 161), at room temperature. Vertical scale 610 ranges from approximately 13% oxygen to 100% oxygen. Flow 161a is received through inlet 161 (not shown), and flow 162a is received through inlet 162 (not shown). Flow 161a is merged with flow 162a into a gas mixture that is received at inlet 11 (not shown) of gas mixing circuit 10 (not shown). As depicted in FIG. 6, the concentration profile of inlet flow 11a may be not uniform. However, as the gas mixture proceeds along flow 10a through the gas mixing circuit 10 (not shown) to, ultimately, outlet flow 15a, and especially along diffusion flow 13a, the concentration profile of the gas mixture gradually becomes more uniform, e.g. the gas mixture transforms from not being substantially uniform at inlet flow 11a, to substantially uniform at outlet flow 15a. In some embodiments, the gas mixture transforms from not being predominantly uniform at inlet flow 11a, to predominantly uniform at outlet flow 15a. In some embodiments, the gas mixture transforms from not being considerably uniform at inlet flow 11a, to considerably uniform at outlet flow 15a. In some embodiments, the gas mixture transforms from not being approximately uniform at inlet flow 11a, to approximately uniform at outlet flow 15a. In some embodiments, the gas mixture transforms from not being practically uniform at inlet flow 11a, to practically uniform at outlet flow 15a.

Concentration profile 15b at the end of outlet 15 (not shown) may be substantially uniform, i.e. the measured range of differences in concentration percentage of oxygen at any point of concentration profile 15b may be less than 8%. In some embodiments, predominantly uniform may be defined as within a 4% deviation from a target and/or average percentage concentration. For example, if a target and/or average oxygen concentration is 60%, then a concentration profile of a gas mixture may be considered predominantly uniform at a particular point along the flow of the gas mixture if the measured concentration percentage of oxygen ranges within −4% and +4% of the target oxygen concentration. In some embodiments, if a target and/or average concentration of a gas or gas component within a gas mixture is defined as a percentage t, then a concentration profile of the gas mixture may be considered considerably uniform at a particular point and/or plane along the flow of the gas mixture if the measured concentration percentages that comprise the concentration profile range between 0.9*t and 1.1*t. In some embodiments, a concentration profile of a gas mixture includes a plurality of sample values representing concentrations, e.g. as a percentage, of a gas and/or gas component in the gas mixture. A gas mixture and/or gas concentration profile may be considered not practically uniform if the sample standard deviation of multiple sample values is about greater than 8, about greater than 10, about greater than 12, or about 14, and practically uniform if the sample standard deviation of multiple sample values is about less than 4, about less than 3, about less than 2.5, or about 2.

Figure 8:
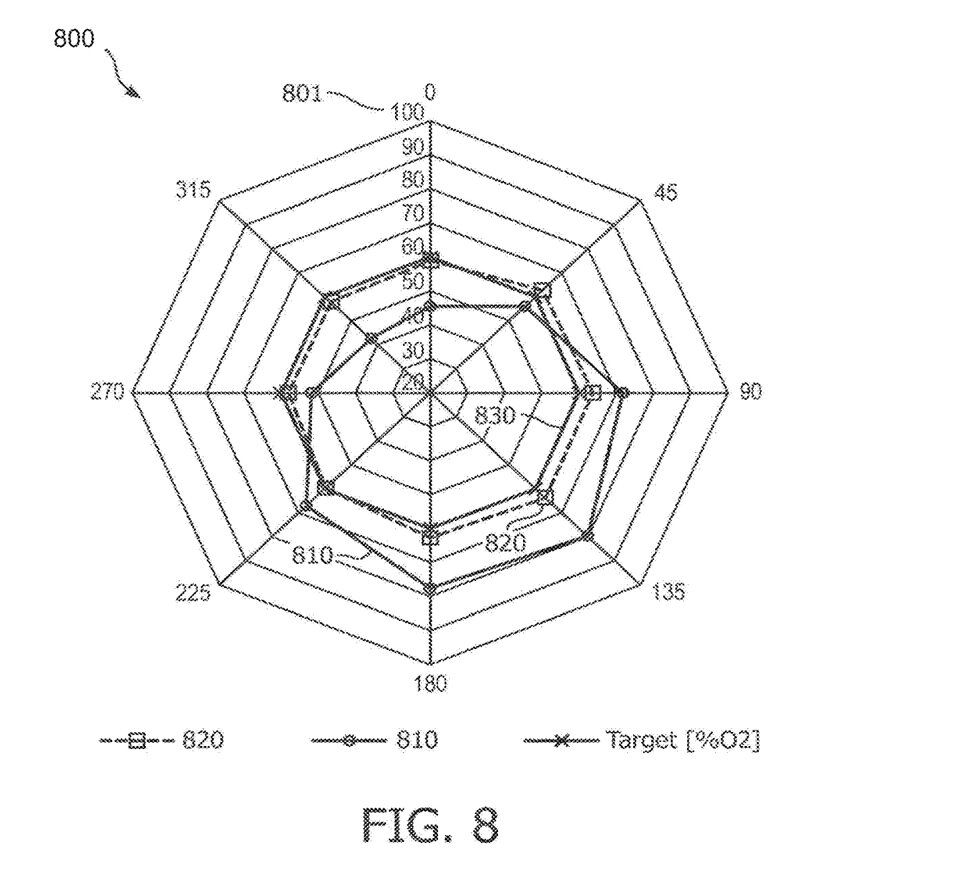
FIG. 8 illustrates concentration profiles of part of a respiratory therapy system.

By way of illustration, FIG. 8 illustrates concentration profiles 800 of part of a respiratory therapy system. FIG. 8 may result by merging and mixing two flows of similar size, such as the flow of oxygen and the flow of air pertaining to FIG. 6. Concentration profiles 810, 820 and 830 may be determined and/or measured by sampling the oxygen concentration 801 near the periphery of the flow of the gas mixture, at 45 degree intervals around the periphery. Concentration profile 830 depicts the target oxygen concentration of 60% oxygen in the gas mixture. Concentration profile 810 depicts the concentration profile at inlet 11 (not shown in FIG. 8) of gas mixing circuit 10 (not shown in FIG. 8). The sample standard deviation of the eight sample values of oxygen concentration of the gas mixture, included in concentration profile 810, is about 14, with measured concentration percentages being 42.4%, 45.4%, 55.9%, 71.5%, 79.6%, 77.6%, 67.6%, and 51.7%. Concentration profile 820 depicts the concentration profile at outlet 15 (now shown in FIG. 8) of gas mixing circuit 10 (not shown in FIG. 8). The sample standard deviation of the eight sample values of oxygen concentration of the gas mixture, included in concentration profile 820, is about 2.5, with measured concentration percentages being 58.6%, 62.1%, 63.4%, 64.0%, 62.8%, 59.5%, 58.3%, and 57.6%. The change in (sample) standard deviation from concentration profile 810 to concentration profile 820 may be about a factor 2, 3, 4, 5, 6, 7, 8, and/or another factor.

Subject interface appliance 184 is configured to deliver the pressurized flow of breathable gas to the airway of subject 106. As such, subject interface appliance 184 may include any appliance suitable for this function. In certain embodiments, pressure generator 140 is a dedicated ventilation device and subject interface appliance 184 is configured to be removably coupled with another interface appliance being used to deliver respiratory therapy to subject 106. For example, subject interface appliance 184 is configured to engage with and/or be inserted into an endotracheal tube, a tracheotomy portal, and/or other interface appliances. In certain embodiments, subject interface appliance 184 is configured to engage the airway of subject 106 without an intervening appliance. In this embodiment, subject interface appliance 184 includes one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

System 100 may include electronic storage 130 comprising electronic storage media that electronically stores information. The electronic storage media of electronic storage 130 includes one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 stores software algorithms, information determined by processor 110, information received via user interface 120, and/or other information that enables system 100 to function properly. For example, electronic storage 130 may record or store operational settings, one or more (breathing) parameters and/or other parameters (as discussed elsewhere herein), pressure levels, information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, and/or other information. Electronic storage 130 may be a separate component within system 100, or electronic storage 130 may be provided integrally with one or more other components of system 100 (e.g., processor 110).

Referring to FIG. 1, user interface 120 of system 100 in FIG. 1 may be configured to provide an interface between system 100 and a user (e.g., user 108) through which the user can provide information to and receive information from system 100. This enables data, results, and/or instructions and any other communicable items, collectively referred to as "information," to be communicated between the user and system 100. An example of information that may be conveyed to user 108 is information regarding the current concentration of oxygen within the gas mixture. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more measurements of the current concentration profile (as discussed elsewhere herein), and/or other information. Electronic storage 130 may be a separate component within system 100, or electronic storage 130 may be provided integrally with one or more other components of system 100 (e.g., processor 110).

System 100 may include sensor 142 configured to generate one or more output signals conveying measurements related to gas and/or respiratory parameters, including one or more of flow, pressure, concentration (e.g. of oxygen), humidity, velocity, acceleration, and/or other parameters. Based on these parameters, system 100 (and/or any constituent components thereof) may be configured to determine one or more breathing parameters, including (tidal) volume, retrograde volume, respiratory rate, breathing period, inhalation time or period, exhalation time or period, peak flow, flow rate, respiration flow curve shape, transition time from inhalation to exhalation and/or vice versa, transition time from peak inhalation flow rate to peak exhalation flow rate and/or vice versa, respiration pressure curve shape, (intentional) gas leak, and/or other breathing parameters. Sensor 142 may be in fluid communication with conduit 182 and/or subject interface appliance 184.

The illustration of sensor 142 as including a single member in FIG. 1 is not intended to be limiting. In certain embodiments sensor 142 includes a plurality of sensors operating as described above by generating output signals conveying information related to parameters associated with the gas breathed by subject 106 and/or the delivery of the gas to subject 106. For example, a breathing parameter may be related to a mechanical unit of measurement of a component of system 100 such as rotor speed, motor speed, blower speed, fan speed, or a related measurement that serves as a proxy for any of the previously listed breathing parameters through a previously known/calibrated mathematical relationship. Resulting signals or information from sensor 142 may be transmitted to processor 110, user interface 120, electronic storage 130, and/or other components of system 100. This transmission can be wired and/or wireless.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of an parameter determination module 111, a pressure generator control module 112, an external supply control module 113, a user interface module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 1 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Parameter determination module 111 is configured to determine one or more gas parameters, breathing parameters, and/or other parameters from the output signals generated by sensor(s) 142. Gas parameters of the (pressurized) flow of breathable gas may include one or more of (peak) flow, pressure, concentration of a gas or gas component, gas composition, temperature, humidity, velocity, acceleration, and/or other gas parameters related to the flow of breathable gas. Breathing parameters may be derived from the one or more gas parameters, and include on or more of tidal volume of the breathing of the subject, respiratory rate, breathing period, inhalation time or period, exhalation time or period, inhalation volume, exhalation volume, peak flow, flow rate of the breathing of the subject, respiration flow curve shape, transition time from inhalation to exhalation and/or vice versa, respiration pressure curve shape, pressure volume loops, flow-volume loops, gas leak, and/or other breathing parameters. Some or all of the stated functionality of parameter determination module 111 may be incorporated or integrated into other computer program modules of processor 110 and/or other components of system 100.

Pressure generator control module 112 is configured to control pressure generator 140 such that one or more gas parameters of the pressurized flow of breathable gas are varied over time in accordance with a respiratory therapy regimen. Pressure generator control module 112 may be configured to control pressure generator 140 to provide the pressurized flow of breathable gas at inhalation pressure levels during inhalation phases, and at exhalation pressure levels during exhalation phases. Parameters determined by parameter determination module 111 (and/or received through sensor 142) may be used by pressure generator control module 112, e.g. in a feedback manner, to adjust ventilator settings/operations. Pressure generator control module 112 may be configured to time its operations relative to the transitional moments in the breathing cycle of a subject and over multiple breath cycles.

External supply control module 113 may be configured to control (external) gas supply 150 such that one or more gas parameters of the pressurized flow of breathable gas received through gas coupler 151 are varied over time in accordance with a respiratory therapy regimen. External supply control module 113 may be configured to control gas supply 150 to provide the pressurized flow of breathable gas at inhalation pressure levels during inhalation phases, and at exhalation pressure levels during exhalation phases. In some embodiments, the pressure and/or flow controlled through external supply control module 113 are substantially constant throughout the respiratory cycle. Parameters determined by parameter determination module 111 (and/or received through sensor 142) may be used by external supply control module 113, e.g. in a feedback manner, to adjust ventilator settings and/or operations. External supply control module 113 may be configured to time its operations relative to the transitional moments in the breathing cycle of a subject and over multiple breath cycles.

User interface module 114 may be configured to control the transfer of communication signals, information, and/or any communicable items between user interface 120 and user 108. For example, user interface module 114 may be configured to communicate, to user 108, information regarding the gas mixture being delivered to subject 106.

Figure 5:
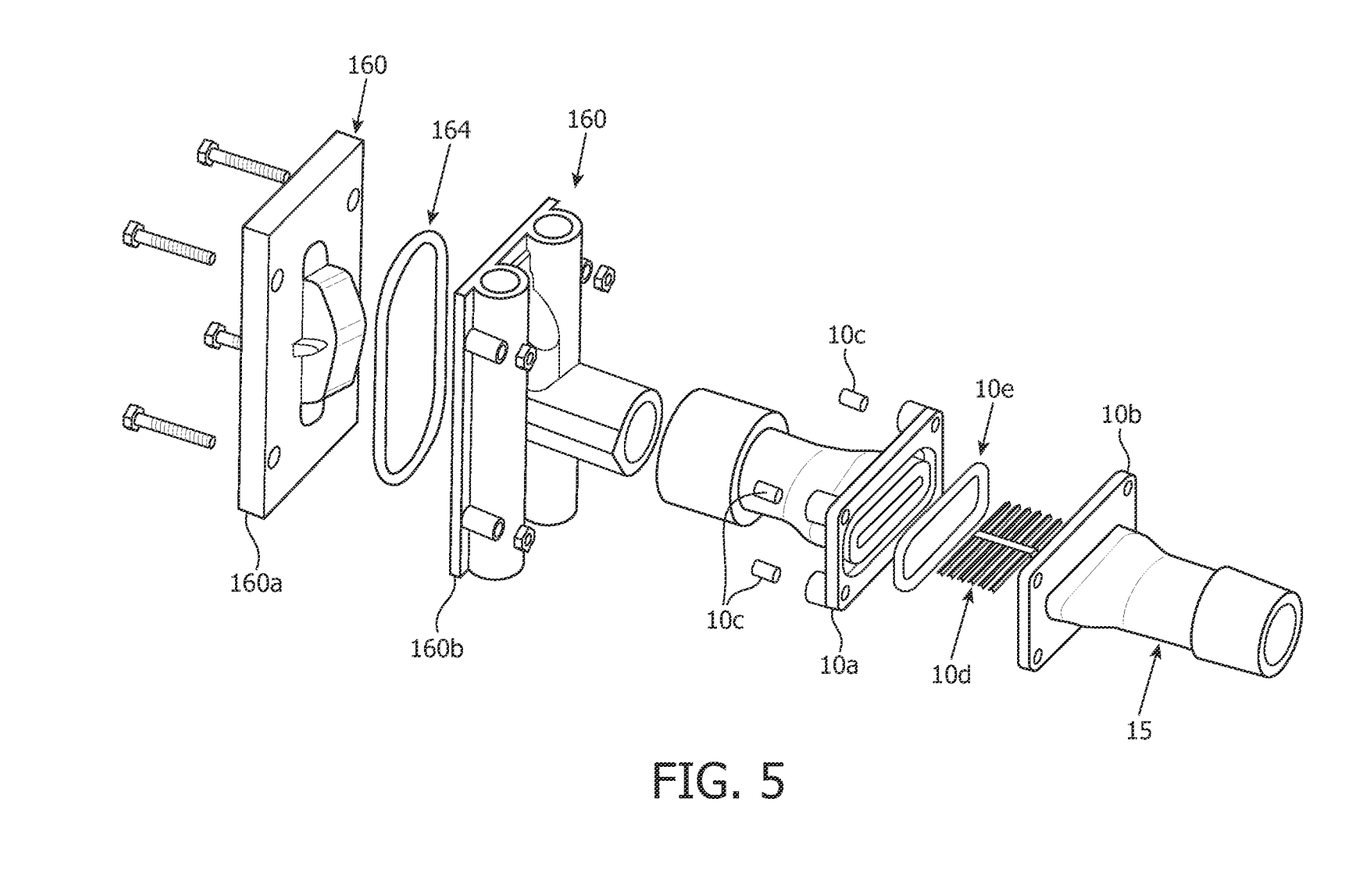
FIG. 5 illustrates an exploded isometric view of part of a respiratory therapy system configured to mix gases.

FIG. 5 illustrates an exploded isometric view of part of an embodiment of system 100 configured to mix two flows of gas into a gas mixture. In some embodiments, system 100 may be constructed as shown in FIG. 5. Gas merging circuit 160 may include first gas merging circuit half 160a, second gas merging circuit half 160b, O-ring 164, and/or other components. First gas mixing circuit half 10a may be fastened to second gas mixing circuit half 10b through (self-clinching) nuts 10c, such that O-ring 10e is integrated within gas mixing circuit 10. In some embodiments, gas mixing circuit 10 may include one or more obstructions 10d, which may include bluff bodies. Obstruction(s) 10d may be configured to promote turbulence within gas mixing circuit 10, at the expense of additional pressure drop across gas mixing circuit 10.

Figure 7:
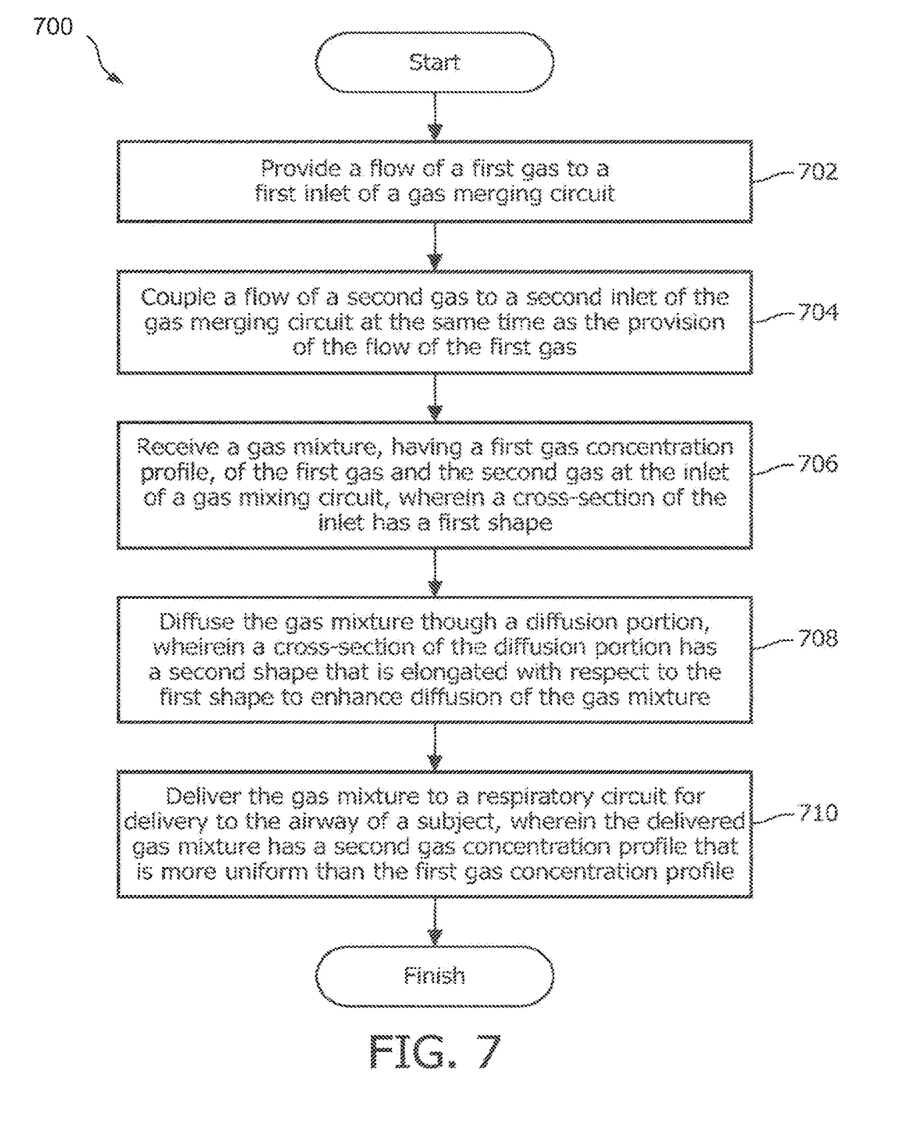
FIG. 7 illustrates a method for mixing gases for delivery to the airway of a subject, in accordance with one or more embodiments.

FIG. 7 illustrates a method 700 for mixing two gases for delivery to the airway of a subject. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/ or software to be specifically designed for execution of one or more of the operations of method 700.

At an operation 702, a flow of a first breathable gas is provided to a first inlet of a gas merging circuit. In one embodiment, operation 702 is performed by a pressure generator similar to or substantially the same as pressure generator 140 (shown in FIG. 1 and described above).

At an operation 702, a flow of a first breathable gas is provided to a first inlet of a gas merging circuit. In one embodiment, operation 702 is performed by a pressure generator similar to or substantially the same as pressure generator 140 (shown in FIG. 1 and described above).

At an operation 704, a flow of a second gas is coupled to a second inlet of the gas merging circuit at the same time as the provision of the flow of the first gas. In one embodiment, operation 704 is performed by a gas coupler similar to or substantially the same as gas coupler 151 (shown in FIG. 1 and described above).

At an operation 706, a gas mixture of the first gas and the second gas, the gas mixture having a first concentration profile, is received at the inlet of a gas mixing circuit, wherein a cross-section of the inlet has a first shape. In one embodiment, operation 706 is performed by a gas inlet similar to or substantially the same as inlet 11 of gas mixing circuit 10 (shown in FIG. 2A-D and described above).

At an operation 708, the gas mixture is diffused through a diffusion portion, wherein a cross-section of the diffusion portion has a second shape that is elongated with respect to the first shape, to enhance diffusion of the gas mixture. In one embodiment, operation 708 is performed by a diffusion portion similar to or substantially the same as diffusion portion 12 (shown in FIG. 2A-D and described above).

At an operation 710, the gas mixture is delivered to a respiratory circuit for delivery to the airway of a subject, wherein the delivered gas has a second concentration profile that is more uniform than the first concentration profile. In one embodiment, operation 710 is performed by a gas outlet similar to or substantially the same as outlet 15 of gas mixing circuit 10 (shown in FIG. 2A-D and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory therapy system configured to mix at least two gases for delivery to the airway of a subject, the respiratory therapy system comprising:
   a pressure generator configured to generate a pressurized flow of a first gas for delivery to the airway of a subject, in accordance with a therapeutic regimen;
   a gas coupler configured to fluidly couple the respiratory therapy system to a gas supply to transfer a second gas from the gas supply through the gas coupler;
   a gas merging circuit configured to merge the first gas from the pressure generator with the second gas from the gas supply into a gas mixture having (i) a percentage concentration of the first gas and (ii) a first gas concentration profile at a cross-section of an output of the gas merging circuit after being merged by the gas merging circuit, wherein the first gas concentration profile at the cross-section of the output of the gas merging circuit includes a first sample standard deviation of a spatial distribution of sample values of percentage concentrations of the first gas; and
   a gas mixing circuit configured to further mix the gas mixture of the first gas with the second gas that has the first gas concentration profile along a flow path formed within the gas mixing circuit, wherein the gas mixing circuit comprises:
   (i) an inlet configured to receive the gas mixture of the first gas and the second gas from the output of the gas merging circuit, wherein a cross-section transverse to a longitudinal axis of the flow path formed within the gas mixing circuit at the inlet has a first cross-sectional shape;
   (ii) a diffusion portion coupled between a first transitional portion and a second transitional portion, wherein the first transitional portion, the diffusion portion and the second transitional portion are configured to further mix the gas mixture of the first gas and the second gas through turbulent diffusion, wherein a cross-section transverse to the longitudinal axis of the flow path formed within the gas mixing circuit at the diffusion portion has a second cross-sectional shape that is elongated along a particular orientation of the second cross-sectional shape with respect to a similar orientation of the first cross-sectional shape to enhance turbulent diffusion of the gas mixture to more uniformly mix the gas mixture as the gas mixture travels through the diffusion portion; and
   (iii) an outlet configured to receive the gas mixture that has been mixed within the diffusion portion, and to guide the gas mixture to a respiratory circuit for delivery to the airway of the subject,
   wherein the gas mixture guided by the outlet has a second gas concentration profile at a given cross-section of the outlet that is more uniform than the first gas concentration profile at the cross-section of the output of the merging circuit, wherein the second gas concentration profile at the given cross-section of the outlet includes a second sample standard deviation of a spatial distribution of sample values of percentage concentrations of the first gas, and wherein the second sample standard deviation comprises a value that is less than half of a value of the first sample standard deviation, and
   wherein the first cross-sectional shape of the cross-section of the flow path at the inlet has a maximum inlet dimension and a minimum inlet width transverse to the maximum inlet dimension, and wherein the second cross-sectional shape of the cross-section of the flow path at the diffusion portion has a maximum diffusion dimension greater than the maximum inlet dimension and a minimum diffusion width, transverse to the maximum diffusion dimension, that is less than the minimum inlet width.

2. The respiratory therapy system of claim 1, wherein the first cross-sectional shape of the cross-section of the flow path at the inlet has a maximum inlet dimension and a minimum inlet width transverse to the maximum inlet dimension, and wherein the second cross-sectional shape of the cross-section of the flow path at the diffusion portion has a maximum diffusion dimension at least twice the maximum inlet dimension and a minimum diffusion width, transverse to the maximum diffusion dimension, that is less than half the minimum inlet width.

3. The respiratory therapy system of claim 1, wherein a cross-section of the second cross-sectional shape is elongated along a horizontal orientation, wherein the gas merging circuit comprises a first inlet configured to receive the first gas and a second inlet configured to receive the second gas, wherein the first inlet is arranged relative to the second inlet according to a vertical orientation, and wherein the vertical orientation is substantially perpendicular to the horizontal orientation.

4. The respiratory therapy system of claim 1, wherein the second cross-sectional shape is elongated along a horizontal orientation, wherein the first gas concentration profile at the cross-section of the output of the gas merging circuit includes a first area and a second area, wherein the first area comprises a highest quartile of concentration of the first gas, wherein the second area comprises a lowest quartile of the concentration of the first gas, and wherein a line through a centroid of the first area and a centroid of the second area has a vertical orientation that is transverse to the horizontal orientation.

5. The respiratory therapy system of claim 1, wherein the gas mixing circuit is configured to mix the first gas with the second gas such that a pressure drop across the gas mixing circuit is less than 10 cm $H_2O$ for a flow rate of the gas mixture of 250 liters per minute.

6. The respiratory therapy system of claim 1, wherein the gas mixing circuit further comprises one or more obstructions disposed within the diffusion portion, wherein the one or more obstructions are configured to promote turbulence within the gas mixing circuit, and wherein the one or more obstructions include bluff bodies.

7. A method for mixing at least two gases for delivery to the airway of a subject, the method comprising:
  providing a flow of a first gas to a first inlet of a gas merging circuit;
  fluidly coupling a second flow of a second gas to a second inlet of the gas merging circuit, at the same time as the provision of the flow of the first gas, wherein the gas merging circuit merges the first gas with the second gas into a gas mixture having (i) a percentage concentration of the first gas and (ii) a first gas concentration profile at a cross-section of an output of the gas merging circuit after being merged by the gas merging circuit, wherein the first gas concentration profile at the cross-section of the output of the gas merging circuit includes a first sample standard deviation of a spatial distribution of sample values of percentage concentrations of the first gas;
  receiving the gas mixture of the first gas and the second gas at an inlet of a gas mixing circuit from the output of the gas merging circuit, wherein a cross-section transverse to a longitudinal axis of a flow path at the inlet has a first cross-sectional shape;
  diffusing, via turbulent diffusion in a gas mixing circuit, the gas mixture from the inlet of the gas mixing circuit through a first transitional portion, a diffusion portion, and a second transitional portion, wherein a cross-section transverse to the longitudinal axis of the flow path at the diffusion portion has a second cross-sectional shape that is elongated along a particular orientation of the second cross-sectional shape with respect to a similar orientation of the first cross-sectional shape to enhance turbulent diffusion of the gas mixture to more uniformly mix the gas mixture as the gas mixture travels through the diffusion portion; and
  delivering, via an outlet of the gas mixing circuit, the gas mixture to a respiratory circuit for delivery to the airway of a subject,
  wherein the delivered gas mixture has a second gas concentration profile at a given cross-section of the outlet of the gas mixing circuit that is more uniform than the first gas concentration profile at the cross-section of the output of the merging circuit, wherein the second gas concentration profile at the given cross-section of the outlet of the gas mixing circuit includes a second sample standard deviation of a spatial distribution of sample values of percentage concentrations of the first gas, and wherein the second sample standard deviation comprises a value that is less than half of a value of the first sample standard deviation, and wherein the first cross-sectional shape of the cross-section of the flow path at the inlet has a maximum inlet dimension and a minimum inlet width transverse to the maximum inlet dimension, and wherein the second cross-sectional shape of the cross-section of the flow path at the diffusion portion has a maximum diffusion dimension greater than the maximum inlet dimension and a minimum diffusion width, transverse to the maximum diffusion dimension, that is less than the minimum inlet width.

8. The method of claim 7, wherein the first cross-sectional shape of the cross-section of the inlet of the gas mixing circuit has a maximum inlet dimension and a minimum inlet width transverse to the maximum inlet dimension, and wherein the second cross-sectional shape of the cross-section of the diffusion portion has a maximum diffusion dimension at least twice the maximum inlet dimension and a minimum diffusion width, transverse to the maximum diffusion dimension, that is less than half the minimum inlet width.

9. The method of claim 7, wherein a cross-section of the second cross-sectional shape is elongated along a horizontal orientation, wherein the first inlet of the gas merging circuit is arranged relative to the second inlet of the gas merging circuit according to a vertical orientation, and wherein the vertical orientation is substantially perpendicular to the horizontal orientation.

10. The method of claim 7, wherein the second cross-sectional shape is elongated along a horizontal orientation, wherein the first gas concentration profile at the cross-section of the output of the gas merging circuit includes a first area and a second area, wherein the first area comprises a highest quartile of concentration of the first gas, wherein the second area comprises a lowest quartile of concentration of the first gas, and wherein a line through a centroid of the first area and a centroid of the second area has a vertical orientation that is transverse to the horizontal orientation.

11. The method of claim 7, wherein the gas mixture is diffused such that a pressure drop across the diffusion portion is less than 10 cm $H_2O$ for a flow rate of the gas mixture of 250 liters per minute.

12. The method of claim 7, wherein the gas mixing circuit further comprises one or more obstructions disposed within the diffusion portion, wherein the one or more obstructions are configured to promote turbulence within the gas mixing circuit, and wherein the one or more obstructions include bluff bodies.

13. A system configured for mixing at least two gases for delivery to the airway of a subject, the system comprising:
    means for providing a flow of a first gas to a first inlet of a gas merging means;
    means for fluidly coupling a gas supply to the system to transfer a second flow of a second gas to a second inlet of the gas merging means, at the same time as the flow of the first gas is provided to the first inlet of the gas merging means;
    the gas merging means for generating, at a merging outlet, a gas mixture of the first gas provided at the first inlet and the second gas provided at the second inlet, wherein the gas mixture has (i) a first gas concentration profile at a cross-section of the merging outlet after being merged and (ii) a percentage concentration of the first gas, wherein the first gas concentration profile at the cross-section of the merging outlet includes a first sample standard deviation of a spatial distribution of sample values of percentage concentrations of the first gas, and wherein a cross-section transverse to a longitudinal axis of a flow path at the merging outlet has a first cross-sectional shape;
    means for diffusing the gas mixture from the merging outlet through a first transitional portion, a diffusion portion, and a second transitional portion, wherein a cross-section transverse to the longitudinal axis of the flow path at the diffusion portion of the means for diffusing has a second cross-sectional shape that is elongated along a particular orientation of the second cross-sectional shape with respect to a similar orientation of the first cross-sectional shape to enhance turbulent diffusion of the gas mixture to more uniformly mix the gas mixture as the gas mixture travels through the means for diffusing; and
    means for delivering the gas mixture to a respiratory circuit for delivery to the airway of a subject,
    wherein the delivered gas mixture has a second gas concentration profile at a given cross-section of the outlet of the means for diffusing that is more uniform than the first gas concentration profile at the cross-section of the merging outlet, wherein the second gas concentration profile at the given cross-section of the outlet of the means for diffusing includes a second sample standard deviation of a spatial distribution of sample values of percentage concentrations of the first gas, and wherein the second sample standard deviation comprises a value that is less than half of a value of the first sample standard deviation, and wherein the first cross-sectional shape of the cross-section of the flow path at the inlet has a maximum inlet dimension and a minimum inlet width transverse to the maximum inlet dimension, and wherein the second cross-sectional shape of the cross-section of the flow path at the diffusion portion has a maximum diffusion dimension greater than the maximum inlet dimension and a minimum diffusion width, transverse to the maximum diffusion dimension, that is less than the minimum inlet width.

14. The system of claim 13, wherein the first cross-sectional shape of the cross-section of the merging outlet has a maximum merging dimension and a minimum merging width transverse to the maximum merging dimension, and wherein the second cross-sectional shape of the cross-section of the means for diffusing has a maximum diffusion dimension at least twice the maximum merging dimension and a minimum diffusion width, transverse to the maximum diffusion dimension, that is less than half the minimum merging width.

15. The system of claim 13, wherein a cross-section of the second cross-sectional shape is elongated along a horizontal orientation, wherein the first inlet of the gas merging means is arranged relative to the second inlet of the gas merging means according to a vertical orientation, and wherein the vertical orientation is substantially perpendicular to the horizontal orientation.

16. The system of claim 13, wherein the second cross-sectional shape is elongated along a horizontal orientation, wherein the first gas concentration profile includes a first area and a second area, wherein the first area comprises a highest quartile of concentration of the first gas, wherein the second area comprises a lowest quartile of concentration of the first gas, and wherein a line through a centroid of the first area and a centroid of the second area has a vertical orientation that is transverse to the horizontal orientation.

17. The system of claim 13, wherein the gas mixture is diffused by the means for diffusing such that a pressure drop across the means for diffusing is less than 10 cm $H_2O$ for a flow rate of the gas mixture of 250 liters per minute.

18. The system of claim 13, wherein the means for diffusing further comprises one or more obstructions disposed within the diffusion portion, wherein the one or more obstructions are configured to promote turbulence within the means for diffusing, and wherein the one or more obstructions include bluff bodies.

* * * * *